US008389277B2

(12) United States Patent
Hanry et al.

(10) Patent No.: US 8,389,277 B2
(45) Date of Patent: Mar. 5, 2013

(54) FORMING CELL STRUCTURE WITH TRANSIENT LINKER IN CAGE

(75) Inventors: Yu Hanry, Singapore (SG); Ong Siew Min, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 381 days.

(21) Appl. No.: 12/682,751

(22) PCT Filed: Oct. 13, 2008

(86) PCT No.: PCT/SG2008/000395
§ 371 (c)(1),
(2), (4) Date: Apr. 12, 2010

(87) PCT Pub. No.: WO2009/048435
PCT Pub. Date: Apr. 16, 2009

(65) Prior Publication Data
US 2010/0216241 A1 Aug. 26, 2010

Related U.S. Application Data

(60) Provisional application No. 60/960,743, filed on Oct. 11, 2007.

(51) Int. Cl.
*C12N 5/071* (2010.01)
(52) U.S. Cl. ........ 435/370; 435/375; 435/382; 435/384; 435/402
(58) Field of Classification Search .................. None
See application file for complete search history.

(56) References Cited

U.S. PATENT DOCUMENTS

| 5,270,192 | A | 12/1993 | Li et al. |
|---|---|---|---|
| 5,459,300 | A | 10/1995 | Kasman |
| 5,624,840 | A | 4/1997 | Naughton et al. |
| 6,197,575 | B1 | 3/2001 | Griffith et al. |
| 6,368,871 | B1 | 4/2002 | Christel et al. |
| 6,653,124 | B1 | 11/2003 | Freeman |
| 2002/0094569 | A1 | 7/2002 | Yu et al. |
| 2002/0182241 | A1 | 12/2002 | Borenstein et al. |
| 2004/0058408 | A1 | 3/2004 | Thomas et al. |
| 2006/0000772 | A1 | 1/2006 | Sano et al. |
| 2006/0011480 | A1 | 1/2006 | Sano et al. |
| 2008/0233607 | A1 | 9/2008 | Yu et al. |

FOREIGN PATENT DOCUMENTS

| WO | 2004/040318 A1 | 5/2004 |
|---|---|---|
| WO | 2004/051231 A1 | 6/2004 |
| WO | 2004/069983 A2 | 8/2004 |
| WO | 2006/011855 A1 | 2/2006 |
| WO | 2006/052223 | 5/2006 |

OTHER PUBLICATIONS

Canadian Intellectual Property Office, "Office Action", dated May 31, 2011 in related Canadian Application No. 2,586,400.
European Patent Office, "Extended European Search Report", dated Jun. 24, 2009, in related European Patent Office Application No. 05805744.9.
European Patent Office, "Examination Report", dated Apr. 6, 2011, in related European Patent Office Application No. 05805744.9.
Tan et al., "Layer-by-layer microfluidics for biomimetic three-dimensional structures", Biomaterials, 2004, pp. 1355-1364, vol. 25, No. 7-8, Elsevier Science Publishers B.V., Barking, GB.
Toh et al., "A Configurable Three-Dimensional Microenvironment in a Microfluidic Channel for Primary Hepatocyte Culture", ASSAY and Drug Development Technologies, 2005, pp. 169-176, vol. 3, No. 2, Mary Ann Liebert, Inc.
Wang et al., "Generation of Three-Dimensional Hepatocyte/Gelatin Structures with Rapid Prototyping System", Tissue Engineering, 2006, pp. 83-90, vol. 12, No. 1, Mary Ann Liebert, Inc.
Ong et al., "A gel-free 3D microfluidic cell culture system", Biomaterials, 2008, pp. 3237-3244, vol. 29, Elsevier Ltd.
Abbott et al., "Biology's New Dimension", Nature, 2003, pp. 870-872, vol. 424, Nature Publishing Group.
Albrecht et al., "Probing the role of multicellular organization in three-dimensional microenvironments", Nature Methods, 2006, pp. 369-375, vol. 3, No. 5, Nature Publishing Group.
Albrecht et al., "Photo- and electropatterning of hydrogel-encapsulated living cell arrays", Lab Chip, 2005, pp. 111-118, vol. 5, The Royal Society of Chemistry.
Zhao et al., "Dendrimer hydrazides as multivalent transient intercellular linkers", Biomaterials, 2008, pp. 3693-3702, vol. 29, Elsevier Ltd.
Griffith, "Emerging design principles in biomaterials and scaffolds for tissue engineering", Annals New York Academy of Sciences, 2002, pp. 83-95, vol. 961, New York Academy of Sciences.
Kim et al., "A microfluidic platform for 3-dimensional cell culture and cell-based assays", Biomedical Microdevices, 2007, pp. 25-34, vol. 9, Springer Science + Bussiness Media, LLC.
Lee et al., "Hydrogels for Tissue Engineering", Chemical Reviews, 2001, pp. 1869-1879, vol. 101, No. 7, American Chemical Society.
Ong et al., "Transient inter-cellular polymeric linker", Biomaterials, 2007, pp. 3656-3667, vol. 28, Elsevier. Plymale et al., "Monitoring simultaneous subcellular events in vitro by means of coherent multiprobe fluorescence", Nature Medicine, 1999, pp. 351-355, vol. 5, No. 3, Nature America Inc.
De Bank et al., "Surface Engineering of Living Myoblasts Via Selective Periodate Oxidation", Biotechnology and Bioengineering, 2003, pp. 800-808, vol. 81, No. 7, Wiley Periodicals, Inc.

(Continued)

*Primary Examiner* — Jim Ketter
(74) *Attorney, Agent, or Firm* — Klarquist Sparkman, LLP

(57) ABSTRACT

In a method of forming a cellular structure, cells and a transient linker are supplied to a volume partially enclosed by a cage. The linker facilitates initial attachment of adjacent cells to form a cell aggregate. The cage defines distributed openings that are sized to retain the cell aggregate. A fluid comprising a cell culture medium is supplied to the volume. The fluid is withdrawn from the volume through the openings. Aggregated cells retained in the volume are cultured to form a cell structure. A cell culturing device is provided which comprises a conduit and a cage in the conduit. A fluid flows in the conduit. The fluid comprises the cells, the transient linker and the cell culture medium. The cage retains aggregated cells formed in the fluid, and defines distributed openings that allow the fluid to flow through.

30 Claims, 14 Drawing Sheets

OTHER PUBLICATIONS

Toh et al., "A novel 3D mamalian cell perfusion-culture system in microfluidic channels", Lab Chip, 2007, pp. 302-309, vol. 7, The Royal Society of Chemistry.

Viravaidya et al., "Development of a microscale cell culture analog to probe naphthalene toxicity", Biotechnol. Prog., 2004, pp. 316-323, vol. 20, American Chemical Society and American Institute of Chemical Engineers.

Kim et al., "A practical guide to microfluidic perfusion culture of adherent mammalian cells", Lab Chip, 2007, pp. 681-694, vol. 7, No. 6.

Kellam et al., "Chemical modification of mammalian cell surfaces", Chem. Soc. Rev., 2003, pp. 327-337, vol. 32.

Saxon et al., "Chemical and biological strategies for engineering cell surface glycosylation", Annu. Rev. Cell. Dev. Biol., 2001, pp. 1-23, vol. 17.

Braet, F., "Isolation, Purification and Cultivation of Rat Liver Sinusoidal Endothelial Cells", Laboratory Investigation, 1994, pp. 944-952, vol. 70, No. 6, The United States and Canadian Academy of Pathology, Inc., U.S.A.

Bhatia, S.N., et al., "Effect of Cell-Cell Interactions in Preservation of Cellular Phenotype: Cocultivation of Hepatocytes and Nonparenchymal Cells", Journal of the Federation of American Societies for Experimental Biology, 1999, pp. 1883-1900, vol. 13.

Brown, D.C. and Richard S. Larson, "Improvements to Parallel Plate Flow Chambers to Reduce Reagent and Cellular Requirements", BMC Immunology, 2001, vol. 2, No. 9, BioMed Central. Available online: <http://www.biomedcentral.com/1471-2172/2/9>.

Chia, et al., "Hepatocyte Encapsulation for Enhanced Cellular Functions", Tissue Engineering (2000); p. 481-495, vol. 6, No. 5, Mary Ann Liebert Inc.

Chiu, D.T., et al., "Patterned deposition of cells and proteins onto surfaces by using three-dimensional microfluidic systems", Proceedings of the National Academy of Sciences, Mar. 14, 2000; p. 2408-2413, vol. 97, No. 6.

Duffy, Ciaran and Richard O'Kennedy, "Determination of 7-Hydroxycoumarin and its Glucuronide and Sulphate Conjugates in Live Slice Incubates by Capillary Zone Electrophoresis", Journal of Pharmaceutical and Biomedical Analysis, 1998, pp. 1279-1284, vol. 17, Elsevier Science B.V.

Kaihara, S., et al., "Silicon Micromachining to Tissue Engineer Branched Vascular Channels for Liver Fabrication", Tissue Engineering, 2001, pp. 105-177, vol. 6, No. 2, Mary Ann Liebert, Inc.

Leclerc, E., et al., "Fabrication of Microstructures in Photosensitive Biodegradable Polymers for Tissue Engineering Applications", Biomaterials, 2004, pp. 4683-4690, vol. 25, Elsevier Ltd.

Levitan, I. et al, "A Chamber to Permit Invasive Manipulation of Adherent Cells in Laminar Flow with Minimal Disturbance of Fluid Flow", Annals of Biomedical Engineering, 2000, pp. 11-84-1193, vol. 28, Biomedical Engineering Society.

Liu, V.A. and S.N. Bathia, "Three-Dimensional Photopatterning of Hydrogels Containing Living Cells", Biomedical Microdevices, 2002, pp. 257-266, vol. 4, No. 4, Kluwer Academic Publishers, The Netherlands.

Ng, S., et al., "Optimization of 3-D Hepatocyte Culture by Controlling the Physical and Chemical Properties of the Extra-cellular Matrices", Biomaterials (2005), pp. 3153-3163, vol. 26., Elsevier Ltd.

Park, J., et al., "Microfabricated Grooved Substrates as Platforms for Bioartificial Liver Reactors", Biotechnology and Bioengineering, Apr. 15, 2005, pp. 632-644, vol. 90, No. 5, Wiley Periodicals, Inc.

Park, T.H. and M. Shuler, "Integration of Cell Culture and Microfabrication Technology", Biotechnology Progress, 2003, pp. 243-253, vol. 19, American Chemical Society and American Institute of Chemical Engineers.

Powers, M.J., et al., "A Microfabricated Array Bioreactor for Perfused 3D Liver Culture", Biotechnology and Bioengineering, 2002, pp. 257-269, vol. 78, No. 3, Wiley Periodicals, Inc.

Powers, M.J., et al., "Functional Behavior of Primary Rat Liver Cells in a Three-Dimensional Perfused Microarray Bioreactor", Tissue Engineering, 2002, pp. 499-513, vol. 8, No. 3, Mary Ann Liebert, Inc.

Takayama, S., et al., "Patterning cells and their Environments Using Multiple Laminar Fluid Flows in Capillary Networks", Proceedings of the National Academy of Sciences (U.S.A.), May 1999, pp. 5545-5548, vol. 96.

Tan, W. and Tejal A. Desai, "Microfluidic Patterning of Cells in Extracellular Matrix Biopolymers: Effects of Channel Size, Cell Type, and Matrix Composition on Pattern Integrity", Tissue Engineering, 2003, pp. 255-267, vol. 9, No. 2, Mary Ann Liebert, Inc.

Torisawa et al., "Multi-channel 3-D Cell Culture Device Integrated on a Silicon Chip for Anticancer Drug Sensitivity Test", Biomaterials, 2005, pp. 2165 2172, vol. 26, Elsevier Ltd.

United States Patent Office, "Office Action", Jul. 21, 2011, in U.S. Appl. No. 11/667,715.

"International Search Report and Written Opinion", mailed Dec. 22, 2008, in PCT patent application No. PCT/SG2008/000395.

"International Preliminary Report on Patentability", Sep. 25, 2009, in PCT patent application No. PCT/SG2008/000395.

Notification of the First Office Action, dated Jul. 10, 2012, issued in corresponding China Patent Application No. 200880118648.

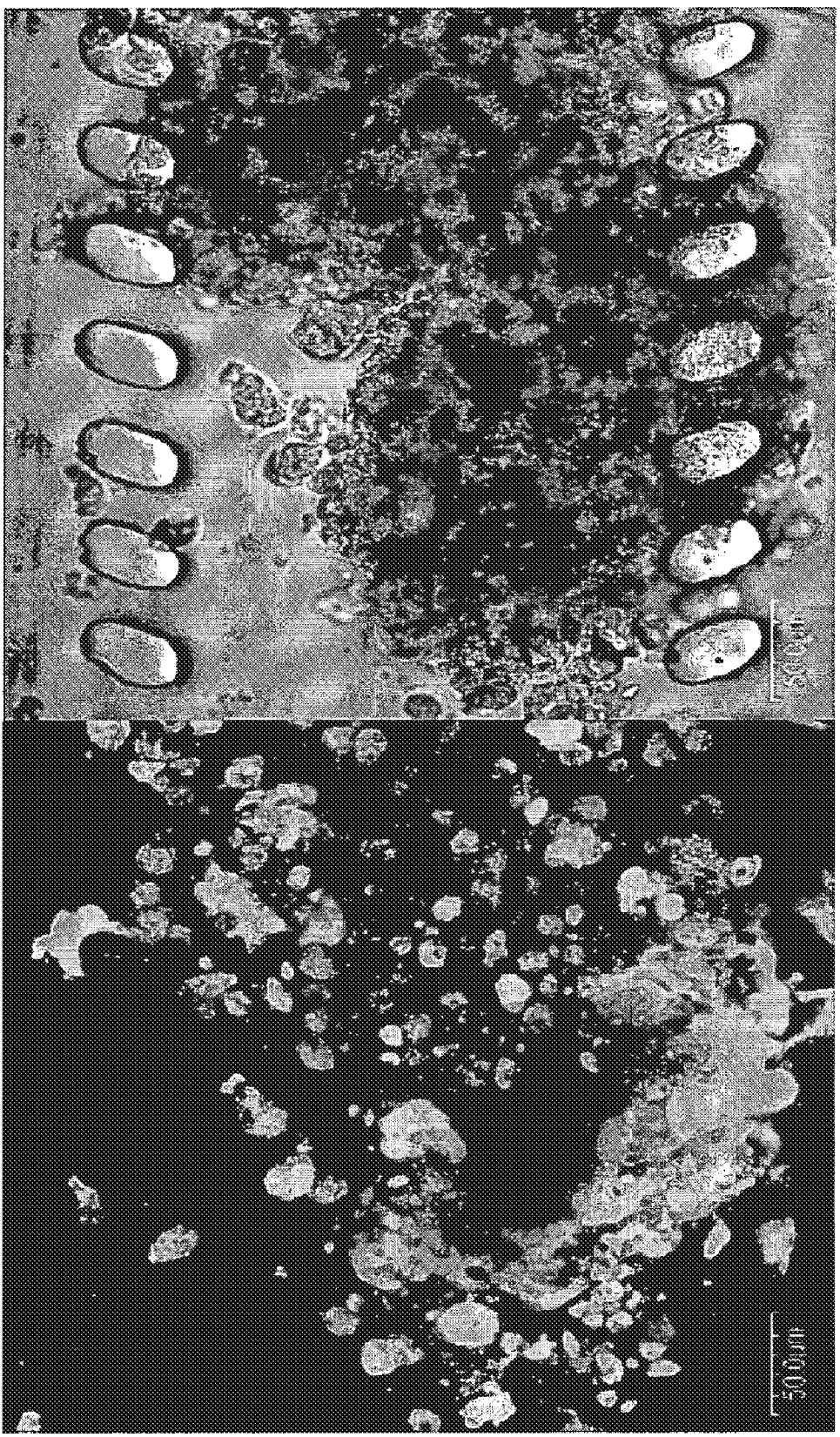

FORMING CELL STRUCTURE WITH TRANSIENT LINKER IN CAGE

CROSS-REFERENCE TO RELATED APPLICATION

This application claims the benefit of U.S. provisional application No. 60/960,743, filed Oct. 11, 2007, the entire contents of which are incorporated herein by reference.

FIELD OF THE INVENTION

The present invention relates to formation of cell structures, particularly to methods and devices for forming three-dimensional (3D) cell structures.

BACKGROUND OF THE INVENTION

Three dimensional (3D) cell structures are important as they can mimic cell behaviors in vivo, more closely than a 2D cell culture. For example, 3D in vitro tissue models with high fidelity to in vivo tissues have important applications in tissue engineering and pathological model development, and can be used to study and test effects and mechanisms of potential therapeutic agents.

A difficulty in conventional techniques of forming 3D cell cultures is to provide efficient transportation of matter, such as a cell culturing medium, through the inner regions of 3D cell structures. As transportation of matter through a cell structure is typically by perfusion, it is more difficult to transport matter through the cell structure when the cell structure has a larger volume. In some conventional techniques, to form micro-scale cell structures, cells are encapsulated in an extra-cellular support, such as in a hydrogel or a thin layer of matrix which provides a 3D extra-cellular matrix (ECM) support for the cell structure. This extra-cellular support forms a barrier which limits transportation of matter to the cells.

SUMMARY OF THE INVENTION

It is thus desirable to form cell structures in an environment that facilitates transportation of matter through the cell structures. It has been discovered that a micro-scale cell structure can be efficiently formed with a transient linker and a cage in a fluid conduit. The transient linker initially links the cells to form cell aggregates but will not form a permanent barrier that limits transportation of matter to and from the cells. The cage retains the aggregated cells but has distributed openings to facilitate transportation of matter through different regions in the formed cell structure. The cage may include a plurality of micro-pillars arranged in a substantially U-shaped pattern, where the gaps between adjacent pillars allow fluid communication but are sized to retain aggregated cells.

According to an aspect of the present invention, there is provided a method of forming a cellular structure. The method comprises supplying cells and a transient linker to a volume partially enclosed by a cage. The linker facilitates initial attachment of adjacent cells to form a cell aggregate. The cage defines distributed openings that are sized to retain the cell aggregate. A fluid comprising a cell culture medium is supplied to the volume. The fluid is withdrawn from the volume through the openings. Aggregated cells retained in the volume are cultured to form a cell structure. The cells may be suspended in the fluid and the linker may be dissolved in the fluid before the fluid is supplied to the volume. A flow of the fluid through the volume may be maintained. The cells in the fluid may have a density of about 5 to about 6 million cells/ml and the transient linker in the fluid may have a concentration of about 6 to about 8 µM. The openings may be distributed to facilitate perfusion of the cell culture medium through the cell structure. The cage may be disposed in a conduit, and the fluid may flow through the conduit. The conduit may comprise a bottom and opposing side walls extending from the bottom. The cage may comprise a plurality of projections extending from the bottom and between the side walls. The projections may comprise micro-pillars. The micro-pillars may be arranged in a substantially U-shaped pattern. The gap between two adjacent micro-pillars may be about 10 to about 50 micrometers. The linker may comprise a polyethyleneimine backbone and hydrazide groups bonded to the backbone. The linker may have a molecular weight of about 2000 to about 20000 Dalton. The cells may comprise HepG2 cells or rat bone marrow stem cells. The cells may comprise an aldehyde group. The cells may comprise cells that have been modified to form aldehyde groups on surfaces of the modified cells. The flow of the fluid may be actuated by applying a withdrawal force downstream of the distributed openings.

According to another aspect of the present invention, there is provided a cell culturing device. The device comprises a conduit; a fluid flowing in the conduit, the fluid comprising cells, a transient linker and a cell culture medium, the linker facilitating initial attachment of adjacent cells to form a cell aggregate; and a cage in the conduit for retaining aggregated cells formed in the fluid, the cage defining distributed openings that allow the fluid to flow through. The cage may comprise a plurality of projections, arranged in a substantially U-shaped pattern. The projections may comprise micro-pillars. The conduit may have a bottom and opposing side walls extending from the bottom, and the projections may extend from the bottom. The cells in the fluid may have a density of about 5 to about 6 million cells/ml and the transient linker in the fluid may have a concentration of about 6 to about 8 µM. The cells may be suspended in the fluid. The linker may be dissolved in the fluid. The linker may comprise a polyethyleneimine backbone and hydrazide groups bonded to the backbone. The linker may have a molecular weight of about 2000 to about 20000 Dalton. The cells may comprise an aldehyde group. The cells may comprise HepG2 cells or rat bone marrow stem cells. The fluid may be actuated by a withdrawal force applied downstream of the distributed openings.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

FIG. 15 is a confocal image of a perfusion cell culture of primary rat bone marrow stem cells in a fluid channel, formed according an embodiment of the present invention;

FIG. 16 is a transmission light image of the cell culture of FIG. 15;

DETAILED DESCRIPTION

Figure 1:
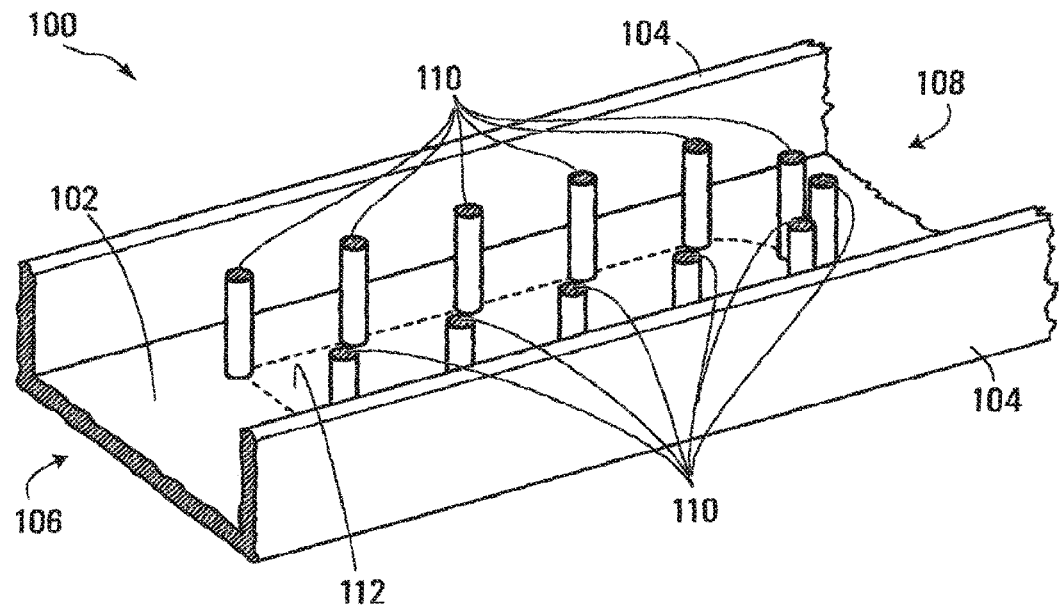
FIG. 1 is a perspective view of a fluid conduit for forming a cell culture structure, exemplary of an embodiment of the present invention.
Figure 2:
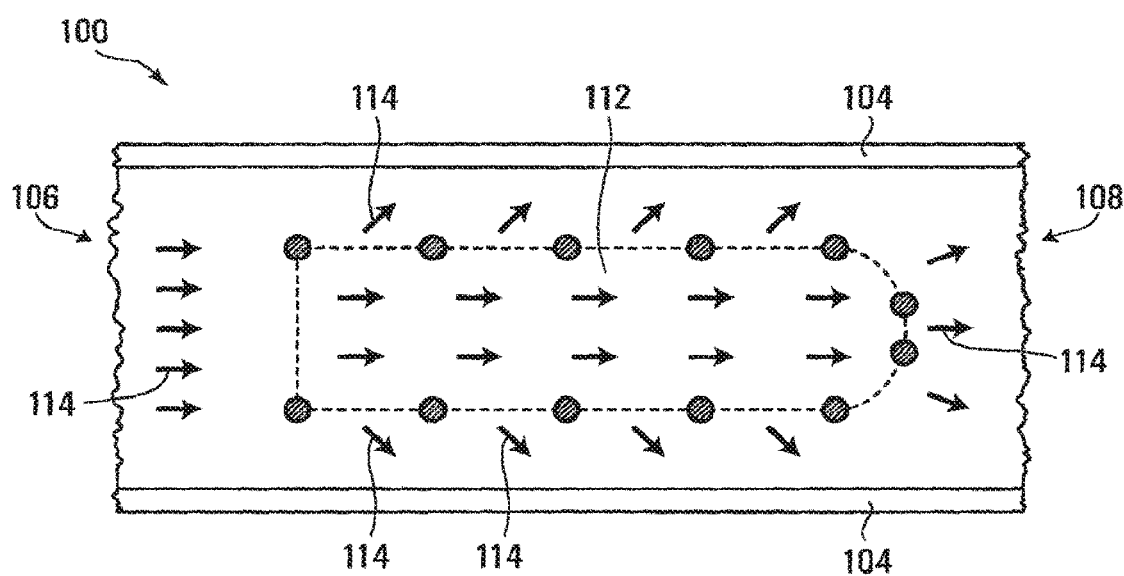
FIGS. 2 and 3 are top plan views of the fluid conduit of FIG. 1 during use.
Figure 3:
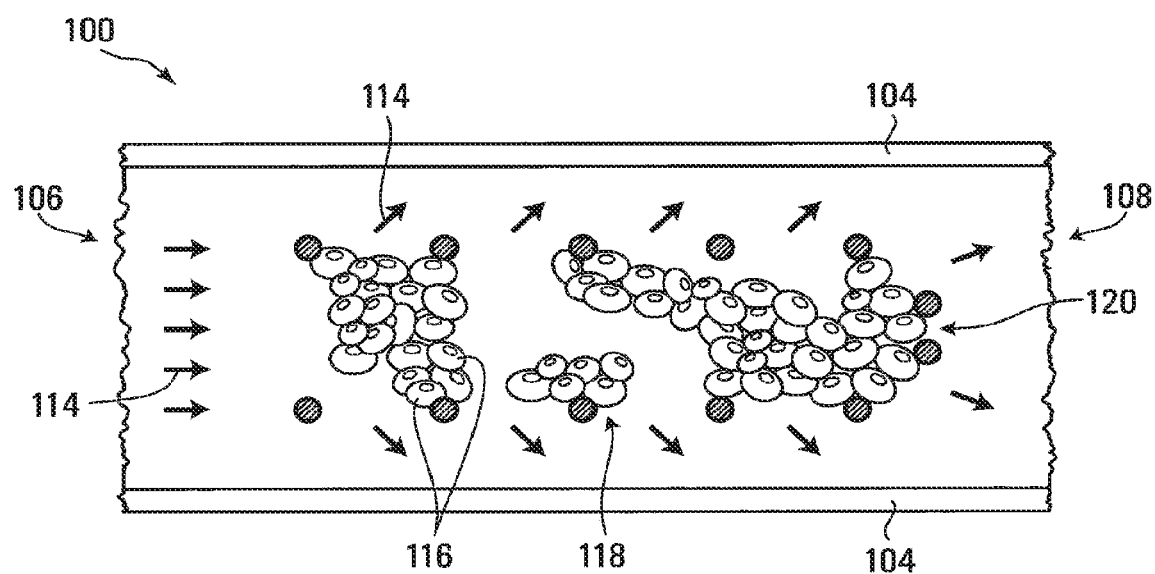

FIGS. 1, 2 and 3 show a fluid conduit 100 for forming and culturing a cell structure, exemplary of an embodiment of the present invention. Fluid conduit 100 may form or be part of a fluidic device for providing a fluid channel in the device. The device may have other components or features not shown in FIGS. 1, 2, and 3 for providing functionalities that may be needed for using the device in a particular application.

Fluid conduit 100 has a bottom 102, opposing side walls 104 extending from bottom 102, an inlet 106, an outlet 108, and a cover (not shown). Inlet 106 is in fluid communication with a fluid source (not shown) for supplying a fluid to conduit 100. Outlet 108 is in fluid communication with a fluid receiver (not shown) for withdrawing the fluid from conduit 100. Inlet and outlet 106, 108 may also be in fluid communication with another fluid supplier or receiver respectively, through different input and output conduits (not shown, but see FIG. 17). The cover covers the top of conduit 100 to provide an enclosure.

The shape and size of the fluid channel defined by conduit 100 may be selected depending on the particular application, including the shape and size of the cell culture structure to be formed. For forming micro-scale cell cultures, the width and height of the fluid channel in conduit 100 may be less than 1 mm. For example, in some embodiments, conduit 100 may have a generally rectangular cross section with a height varying from about 50 to about 500 micrometers.

Conduit 100 may be formed of any suitable material depending on the particular application. For example, bottom 102 and side walls 104 (and the top) may be formed of glass, plastic or a polymer material, or a combination thereof. Suitable polymers may include polycarbonate, polyacrylic, thick-photo resist epoxy resin (e.g. compounds in the SU-8 series from MicroChem Inc., MA, US), polyoxymethylene, polyamide, polybutylenterephthalate, polyphenylenether, polydimethylsiloxane (PDMS), mylar, polyurethane, polyvinylidene fluoride (PVDF), PMMA (polymethyl methacrylate, flourosilicone, or combinations and mixtures thereof. The polymer may be formed using a suitable polymerisable material, which may include monomers, oligomeric building blocks, or any suitable precursor molecules. Different parts of conduit 100 may be formed of the same or different materials.

A plurality of micro-pillars 110 are disposed in conduit 100, which are arranged in a substantially U-shaped pattern and spaced from side walls 104. The open end of the U-shaped pattern faces inlet 106 and the partially-closed-end of the U-shaped pattern faces outlet 108. The gaps between adjacent micro-pillars 110 may be in the range of about 10 to about 50 micrometers. The size of the gaps may be selected to provide a desired perfusion rate through the gaps, as will be further explained below. Micro-pillars 110 may have any suitable cross-sectional shape. The width of micro-pillars 110 may vary, such as in the range of 10 to 50 micrometers. The height of the pillars may be selected depending on the desired cell structure to be formed. In some embodiments, for example, the pillar height may vary from about 10 to about 500 micrometers. In some embodiments, the pillar may extend over the full height of conduit 100.

The micro-pillars may be formed from the same material as that of conduit 100 or a different material.

Micro-pillars 100 define a partially enclosed volume or cell-growth region 112, as delineated by the dash lines in FIGS. 1 and 2.

Optionally, pillars 100 may extend to the top cover of conduit 100. Alternatively, cross-bars (not shown) may be provided to connect the top ends of opposing pairs of pillars 110, and the cross-bars may be spaced from the top cover of conduit 100.

In one embodiment, bottom 102 is made of glass, and the other parts of conduit 100 including side walls 104, pillars 110, and the top cover are formed from the same polymer. Side walls 104, pillars 110, and the top cover may be formed as an integral unit. In this case, pillars 110 extend from the top cover down to the glass bottom 102. The polymeric portion of conduit 110 may be formed by molding. The mold may be a microfabricated silicon mold. The polymeric portion may be tightly attached to the glass bottom 102 to form an enclosed fluid channel. The polymer and glass may be attached to each other by permanent chemical bonding or using a removable fastener such as clamps.

In another embodiment, conduit 100 may as a whole be formed of an integrated unit. The unit may be formed of a plastic, polymer, or the like.

Fluid conduit 100 and micro-pillars 110 may be fabricated using any suitable micro-fabrication technique. The surfaces of fluid conduit 100 and micro-pillars may be treated using known techniques to improve performance in a given application. For example, fluid conduit 100, including micro-pillars 110, may be fabricated using a micro-fabrication technique such as micromachining, replica moulding, soft lithography, reactive ion etching (RIE), or deep reactive ion etching (DRIE), or the like.

In one embodiment, conduit 100 may be formed using polydimethylsiloxane (PDMS). A silicon template may be first formed by deep reactive ion etching. The PDMS material is then molded in the silicon template. The molded PDMS structure may then be oxidized in oxygen plasma, such as for about 1 minute, to chemically bond the PDMS structure to a cover plate (not shown), such as a glass cover slip. The device may be sterilized before use.

In use as better illustrated in FIGS. 2 and 3, a fluid 114 is caused to flow through conduit 100 and cell growth region 112.

Fluid 114 contains a cell culture medium and a transient linker for initially linking the cells to form cell aggregates.

The transient linker will only temporarily attach to the cells and will dissociate from the cells after the adjacent cells form cell aggregates. The linker may be a transient inter-cellular polymeric (TIP) linker. The linker may be dissolved in fluid 144. Cells 116 for forming a desired cell structure are suspended in fluid 114. Fluid 114 may include a carrying solvent for dissolving and carrying the TIP and other ingredients therein. Fluid 114 may be prepared using any suitable preparation technique known to persons skilled in art.

The cell culture medium may contain any suitable material(s) for culturing the particular cells used, as can be appreciated by persons skilled in the art. For example, culture medium may include the nutrients required or desirable for cell growth and culture. For example, the cell culture medium may contain Dulbecco's modified Eagle medium (DMEM), Minimum Essential Medium (MEM), F-10 Nutrient Mixture, F-12 Nutrient Mixture, medium developed by Roswell Park Memorial Institute (RPMI medium), Iscove's Modified Dulbecco's Medium (IMDM), glucose, fetal calf serum (FCS), penicillin/streptonmycin, $CO_2$, growth factors, or other substances.

Cells 116 may be cells that can form cell aggregates through a transient linker, and may include one or more types of cells. For example, cells with sialic acid residues, which can be modified by $NaIO_4$, may be suitable. In some embodiments cells with a higher expression of sialic acid may be used. For example, cell lines such as HepG2 human liver cell line, A549 human lung epithelial cell line, HeLa human cervical cell line, human glioma cell lines U87 and U251, or the like may be suitable. Primary cells such as rat bone marrow mesenchymal stem cells and porcine hepatocytes may also be suitable.

The cells may be selected so that they can be seeded in cell growth region 112 as fluid 114 flows through conduit 100. Cells 116 may be surface-modified so that they will aggregate through the transient linker. For example, cells 116 may be cells that contain, or have been modified to contain, aldehyde groups. Cells 116 may be modified from HepG2 cells (human liver cell line), primary rat bone marrow stem cells (BMSC), A549 human lung epithelial cell line, HeLa human cervical cell line, human glioma cell lines U87 and U251, primary porcine (pig) hepatocytes, or other types of cells.

For culturing HepG2 and BMSC cells, the cell culture medium may include DMEM, 10% FCS and glucose. The glucose content in the cell culture medium may be higher for HepG2 cells, e.g. about 4.5 g/L; and lower for BMSC cells, e.g. about 1.0 g/L.

In one embodiment, it may be desirable to prevent substantial attachment of the cells to the wall surfaces, so that a desired flow rate may be maintained in conduit 100. Attachment may be avoided by either selecting cells that do not attach to the particular wall surfaces or adjusting the fluid flow rate in conduit 100 so that substantial attachment does not occur.

The culturing medium may be osteogenic and may be prepared from a basal medium with 100 nM dexamethasone, 0.05 mM ascorbic acid 2-phosphate and 10 mM β-glycerophosphate.

The transient linker is selected so that it can initially link cells 116 to attach them to each other and form cell aggregates 122. The linker may be selected so that it can establish immediate contact between cells and cause the cells to aggregate to form 3D cellular aggregates. The linker molecules are only temporarily bonded with cells 116 and can dissociate from attached cells after the cells have attached to each other. The half-life of the linker attached to the cell surface may be in the range of about 1 to about 5 days. In one embodiment, the half-life may be about 12 hours or shorter.

For example, for cells with surface aldehyde groups, the linker may contain hydrazide terminal groups, which can react with the aldehyde groups to cause aggregation of the cells. In one embodiment, hydrazide groups may be conjugated or bonded to a polymer backbone such as a polyethyleneimine (PEI) backbone. In different embodiments, other linear polymeric linkers, dendrimer linkers, two-step linkers, or the like, may be used. Some suitable transient linkers are disclosed in, for example, Zhao et al., "Dendrimer hydraides as multivalent transient inter-cellular linkers," *Biomaterials*, 29 (2008) 3693-3702; and De Bank et al., "Surface engineering of living myoblasts via selective periodate oxidation," Biotechnology and bioengineering, vol. 81, 2003, pp. 800-808.

A transient linker will dissociate from the cells after the cells have formed aggregates. Conveniently, the transient linker will not form a permanent barrier around the cells. This allows efficient mass transportation to and from the cells. Further, this allows the cells to establish natural cell-cell interaction, to secrete ECM, and to establish cell-matrix interaction, which may be desired for a 3D inter-cellular support.

The linker may be based on non-toxic low molecular-weight PEI. In one embodiment, the linker may have a molecular weight from about 2000 to about 20000 Dalton. The primary amine groups on the PEI arms may be modified to yield hydrazides, which can react with the aldehyde handles on chemically modified cell surfaces to aggregate cells. The linker may be able to reside transiently on cell surfaces with a half-life of about two days. The linker may be selected to allow anchorage-dependent cells to produce their own native environment for 3D support without incorporating exogenous biomaterials that potentially hinders mass transport. As such, the cells can secrete and accumulate their own ECM for support.

Some cells need to be supported by, or anchored to, a substrate to survive, grow and multiply, which are referred to as anchorage-dependent cells. For example, mammalian cells (primary cells and cell lines) are anchorage dependent. Anchorage-dependent cells may be conveniently used in an embodiment of the present invention, as once the cells have aggregated and been confined in the cell-growth region, they are supported by neighboring cells. Thus, it is not necessary to anchor the cells to an external matrix support such as gels.

The temperature of the fluid may be maintained at a level suitable for culturing the particular cells. In one embodiment, the temperature may be at about 37° C. The temperature in conduit 100 may be controlled using a heating device (not shown) and a temperature controller (not shown). In some embodiments, a heater (not shown) may be embedded in the fluidic device on which conduit 100 is provided.

The flow rates of the fluid flow through conduit 100 are controlled to allow cells 116 to form cell aggregates 118 initially linked by the TIP linker. The flux (the rate of fluid flow per unit area) should be selected to reduce or minimize the impact forces created by the fluid flow on the cells while maintaining sufficient supply of cell culture medium to aggregated cells trapped by micro-pillars 110, in order to maintain viability of the cells. In some embodiments, it may reduce the flow impact if the fluid flow is actuated by applying a withdrawal force downstream of the distributed openings defined by micro-pillars 110. For example, an active withdrawing force may be applied through outlet 108, such as using a fluid pump, instead of applying an actuating force at inlet 106.

It should be understood that the local flux of fluid flow in conduit 100 may not be uniform and may vary in different regions in the channel and at different times. For example, as cell aggregates accumulate in cell growth region 112, the fluid flow inside cell growth region 112 or through the gaps between micro pillars 110 may slow down with time. If a constant overall flow rate through conduit 100 is maintained, the fluid flow outside cell growth region 112 may become faster with time. However, in some embodiments and applications, it is still possible to control the mass transportation or diffusion rate in cell growth region 112 or in the gaps between pillars 110 by adjusting the overall flow rate or flux through conduit 100.

As can be understood, a higher flux may provide faster diffusion in the growth region, but it may also increase the shear stress on the cells. Therefore, the overall flux may be adjusted and optimized to achieve a desired balance.

The flow rate or flux, and other operational parameters, may be optimized so that the in situ formed cellular aggregates are large enough to be confined by pillars 110, but small enough to prevent clogging of the fluidic channel. The sizes of the cellular aggregates may be modulated by cell density and the inter-cellular linker concentration in the fluid. In some embodiments, the cell density may be about 5 to about 6 million cells/ml and the inter-cellular linker concentration may be about 6 to about 8 μM. In one embodiment, the cell density may be about 6 million cells/ml and the inter-cellular linker concentration may be about 6 μM. If the cell density and linker concentration are too high, substantial clogging may occur at inlet 106. If the cell density and linker concentration are too low, aggregation of cells may be too slow to efficiently trap cells in cell growth region 112.

The gaps between micro-pillars 110 have sizes that are selected to allow fluid 114 and individual cells 116 to flow through, but to retain cell aggregates 118 within cell-growth region 112. Gaps in the range of about 10 to about 50 micrometers have been found to be suitable for some cells.

As fluid 114 flows through conduit 110 and through the gaps between micro-pillars 110, cell aggregates 118 continue to grow and eventually form a cell structure 120, with a shape and dimensions generally defined by the locations and shapes of micro-pillars 110 and conforming to cell-growth region 112. As can be appreciated, micro-pillars 110 can be used to confine the cellular aggregates to form cellular constructs of consistent dimensions.

Cell structure 120 may be cultured for a desired period of time, such as up to a few weeks, depending on the particular application. The contents of input fluid 114 and cell culture medium may be adjusted or varied during different stages of the formation and culturing process.

The cell growth in conduit 100 may be observed or monitored. For example, images of the cell aggregates or cell structure may be taken during culturing. For this purpose, at least one side of conduit 100 may be transparent. Images of the cells may be obtained using any suitable technique, such as confocal imaging, transmission light imaging, SEM, or the like.

For imaging, labeling or other purposes, the cells may be stained, such as by F-actin staining, immunostaining of E-cadherin, von Kossa staining, or the like. Staining may be performed in situ, by changing the contents of input fluid 114, including adding appropriate staining materials to input fluid 114.

The cell culture medium used in the cell culturing process may be optionally re-circulated. A closed-loop circulation system (not shown) may be provided and a multi-channel peristaltic pump may be used to circulate the fluid carrying the cell culture medium.

Images and test results of representative cell aggregates and cellular structures formed according to the process described above are shown in FIGS. 4 to 16, as further described below.

As can be appreciated, the openings or gaps between micro-pillars 110 can be conveniently utilized to perfuse the culture medium through various regions in cellular structure 120 to enhance mass transport to and in the structure.

Effectively, micro-pillars 110 form a cage in fluid conduit 100 for retaining aggregated cells 118 formed in fluid 114.

In other embodiments, the cage for retaining aggregated cells may be formed differently. For example, the cage may be formed of pillars, bars, wires, or the like, or a combination thereof. The cage may have one or more open sides. In any case, a volume is partially enclosed by the cage. This volume will substantially define the shape of the cell structure formed from the retained cells. The cage should define distributed openings to allow fluid to flow through, and to facilitate perfusion of matters through the volume. However, at least the openings from which the fluid is withdrawn from the cage should be sized to retain aggregated cells. The distributed openings may be provided on two or more sides of the cage. The cage may be shaped so that the enclosed volume has a desired shape. In some embodiments, the cage may have an open side, as illustrated in FIG. 1. In other embodiments, the cage may be at least partially closed on all sides. One or more sides of the cage may be completely closed (see e.g. bottom 102 of conduit 100 in FIG. 1). As can be appreciated, the cells, transient linker and cell culturing medium may be supplied to the enclosed volume through distributed openings of a partially-closed side or through an open side of the cage. In some embodiments, the input fluid may be supplied to the volume through an opening at the bottom or at the top of the cage.

In some embodiments, the cage may be formed of a rigid material. In other embodiments, a portion of the cage may be formed of a flexible material. For example, a side of the cage may be formed of a flexible material, such as a net or a membrane. In some applications, the net or membrane may have a pre-defined profile when pressured by the fluid flow and the aggregated cells retained in the cage.

The cage may have a fully or partially closed top.

The cage may be formed or placed in a conduit. The conduit may have the shape of a channel or a chamber, or the like. The sides of the cage with distributed openings may be spaced away from walls of the conduit to allow efficient fluid communication through the openings. The cage may be immersed fully or partially in the fluid carrying the cell culturing medium.

As now can be appreciated, the arrangement illustrated in FIGS. 1 to 3 may be modified and still achieve some of the benefits or advantages mentioned herein.

Figure 17:
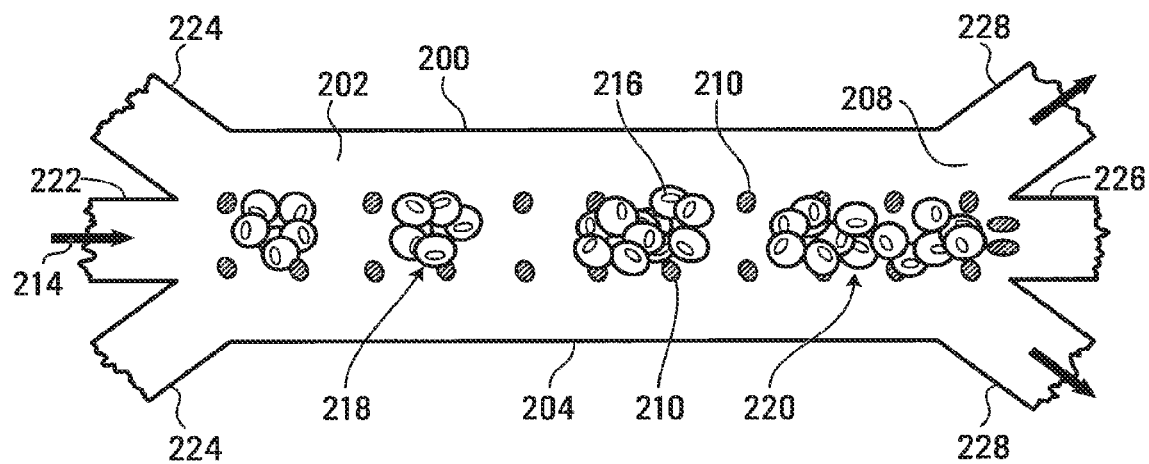
FIG. 17 is a schematic diagram illustrating an alternative fluid conduit for forming a cell culture, exemplary of an embodiment of the present invention.

For example, FIG. 17 shows a fluid conduit 200, with bottom 202, side walls 204, inlet 106, outlet 208, and pillars 210. As for fluid conduit 100 described earlier, a fluid 214 flows through conduit 200. Cells 218 thus form cell aggregates 218 and eventually a cell structure 220. Inlet 206 is in communication with three input conduits, a central conduit 222 and two side conduits 224. Similarly, outlet 208 is in communication with three output conduits, a central conduit 226 and two side conduits 228.

In one embodiment, conduit 200 may have a length of about 10 mm, a width of about 0.6 mm, and a height of about 0.1 mm. Each micro-pillar 210 may have an elliptical cross-section as shown, with the long axis being about 0.5 mm and the short axis being about 0.03 mm. The gaps between adjacent pillars may be about 0.02 mm wide. The distance between the closed end and the open end of the U-shaped pattern may be about 0.2 mm. For this arrangement, the cell density in the seeding fluid may be about 1.5 to about 10 million cells/ml, depending on the cell size. With larger cells, the optimal cell density may be lower.

Elliptical pillars may be advantageous in some applications. However, the pillars may have other cross-sectional shapes in different applications or embodiments.

In use, central conduit 222 may be connected to a cell reservoir (not shown) for supplying cells 216 to conduit 200. Side conduits 224 may be connected to a source of the culture medium for supplying the culture medium to conduit 200. The transient linker may be dissolved in the culture medium. A 4-way valve (not shown) may be provided at inlet 206 for controlling fluid flow and feeding different materials to conduit 200. For example, the valve connected to central conduit 222 may be initially open and then closed after sufficient cells have been supplied to conduit 200.

When cells are being supplied to conduit 200, fluid 214 may be withdrawn from conduit 200 through side conduits 228, such as using a syringe pump (not shown). During culturing of cell structure 220, fluid 214 may be withdrawn from all of conduits 226 and 228.

In a further variation of the embodiment shown in FIG. 1, micro-pillars 110 may be replaced by a cage structure that defines a partially enclosed volume and distributed openings. For example, instead of pillars, a cage wall with spaced slots or openings therein may be provided, as illustrated in FIG. 18.

Figure 18:
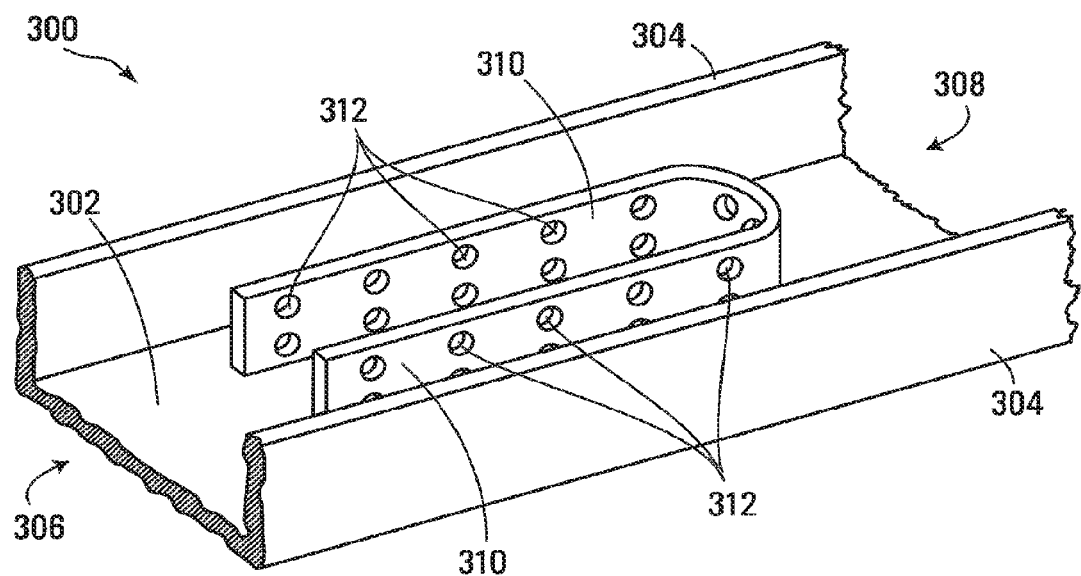
FIG. 18 is a perspective view of a further fluid conduit for forming a cell culture, exemplary of an embodiment of the present invention.

The fluid conduit 300 shown in FIG. 18 is similar to fluid conduit 100 of FIG. 1, having a bottom 302, side walls 304, inlet 306 and outlet 308. The cage wall 310 is provided to replace pillars 110 for retaining aggregated cells. Distributed openings 312 are provided in wall 310 to allow the culture medium to flow through.

In another embodiment, the cage structure may include a fence-like screen or another type of filtering device for retaining aggregated cells while allowing fluid to be withdrawn through the screen or filtering device.

The micro-pillars may also be replaced with other projections extending from the bottom wall of the conduit. For example, micro-pillar'arrays and the techniques for fabricating micro-fluidic devices disclosed in WO 2006/052223 to Yu et al., entitled "Cell Culture Device" and published 18 May 2006, may be modified and adapted for use in forming a suitable device used in an embodiment of the present invention. The contents of WO 2006/052223 related to fabrication of a fluidic device are incorporated herein by reference.

The conduit or channel in which the cage is placed may have different shapes and sizes in different embodiments. For example, it is not necessary that side walls 104 are parallel.

In some embodiments, the conduit may have the shape of a chamber. The chamber may have a generally rectangular, cylindrical or spherical shape. The conduit may also be shaped or sized to accommodate other fluidic elements or devices in addition to the retention cage. The inlet and outlet of the conduit may be provided at any desired locations in the chamber. Fluid ports may also be provided in a wall, such as the bottom, side or top wall, of the conduit to provide alternative or additional inlet/outlet for fluid communication.

To promote formation of cell aggregates using the transient linker, the cells may have, or modified to have, reactive handles on cell surfaces. The transient linker may have corresponding terminal groups for reacting with the reactive handles to "glue" the cells together. The cell surfaces may be modified genetically, via enzymatic treatment, or chemically to generate the reactive handles. Exemplary techniques for modifying cell surfaces are disclosed for example in B. Kellam et al., "Chemical modification of mammalian cell surfaces," *Chem. Soc. Rev.*, 2003, vol. 32, pp. 327-337; E. Saxon et al.; "Chemical and biological strategies for engineering cell surface glycosylation," *Annu. Rev. Cell. Dev. Biol.*, 2001, vol. 17, pp. 1-23; S-M. Ong et al., "Transient inter-cellular polymeric linker," *Biomaterials*, 2007, vol. 28, pp. 3656-3667 (hereinafter referred to as "Ong"), the entire contents of each of which are incorporated herein by reference.

A suitable technique for forming a TIP linker is disclosed in Ong. Other TIP linkers or techniques for forming the TIP linker may also be used.

The embodiments and modification discussed herein are for illustration purposes and are not exhaustive. Other modifications are also possible.

The exemplary embodiments described herein can be advantageously used in many applications.

For example, with the combined use of a transient linker and a micro-pillar array, a 3D cellular structure may be formed quickly, such as within about 5 minutes, and with a precise shape and dimension. The formation process can be relatively easy to perform.

As no permanent extra-cellular matrix or bulk material is used to support the cells, sufficient and efficient transportation of matter through different regions in the cell structure is possible. Continued perfusion through the cell structure both during and after formation is possible due to fluid communication through the gaps between the pillars. The absence of a permanent external support such as a hydrogel matrix that encapsulates the cells and the continued fluid flow allow transport of matters such as oxygen and nutrients to the cells and transport of matters such as metabolic wastes from the cells.

The improved mass transport can be useful for delivery of biological agents to a cellular construct during certain applications, such as in drug testing or biological studies.

A high level of biomimicry may be achieved by allowing the cells to secrete and accumulate their own ECM to produce a native microenvironment without incorporating exogenous biomaterials and utilizing perfusion culture that mimics in vivo vascularization. A higher biomimicry can potentially assist the acquisition of more predictive results from in vivo cellular responses, such as in drug testing or biological studies.

A micro-scale 3D cellular structure formed according an embodiment of the present invention can exhibit many advantages over macro-scale cell structures. For example, the micro-scale 3D cellular structure is more compact in size, may have a higher disposability, can provide faster and parallel analyses, and can reduce the reagent volume required in many applications.

Embodiments of the present application may be used with a biomimicry microchip for drug testing applications. Various tissues may be produced by aggregating one or more cell types in a micro-channel. The use of a transient inter-cellular linker in place of permanent hydrogels for cellular support allows the cells to secrete and accumulate native ECM for support rather than relying on exogenous biomaterials. This cell construct therefore better mimics in vivo cell behaviors.

Multiple fluid channels may be provided to provide high-throughput, such as in drug testing. The micro-channels can be connected to gradient generators to enable simultaneous testing of a range of concentrations of drugs on the cellular structures in different micro-channels. The gradient generator can be designed to be linear, sigmoidal, or exponential, thus providing versatility depending on the user's needs. Such multiplexibility may be useful for modifying existing integrated fluidic circuits to provide efficient manipulation of fluids for high throughput drug testing applications.

Multiple fluid chips may be connected sequentially to perform a method described herein. Different chips may be used to culture different cell types, representing different tissue analogues. Alternatively, different cell types can be cultured in different chambers connected by micro-fluidic channels on a single chip. Therapeutic agents can be circulated through the tissue analogues and their effects at a systemic level can be assayed. Such an arrangement is potentially beneficial for evaluating candidates of therapeutic agents based on a systemic response, which is an order higher than a tissue response. This has potential usage in many different microfluidic devices.

With a transparent conduit material (such as a glass-bottom), the micro-meter scale 3D cell culture formed in the micro-channel can be readily imaged with existing imaging modalities at high resolution. For example, the cell culture may be imaged using phase contrast microscopy, confocal laser scanning microscopy, or two-photon laser microscopy. This enables real-time imaging of cells cultured in a physiological 3D microenvironment, e.g., for the study of various dynamic cellular processes such as epithelial cells polarization, protein trafficking, endocytosis, transcytosis, proliferation, apoptosis, or the like. In particular, it allows high-content screening of single cells in a 3D microenvironment for various applications, including drug testing. Embodiments of the present invention can allow imaging of mammalian cells cultured in 3D while controlling the micro-environmental fluid flow around the cells.

Embodiments of the present invention may also be used to model various in vitro disease developments, such as cancer development, liver and lung fibrosis, or viral infection. By introducing different cell types, or disease-causing agents, a series of models representing different stages of a disease prognosis can be developed. Such models are useful for studying the underlying mechanisms of disease development and testing potential therapeutic agents for disease treatment.

EXAMPLES

Example I

The cell surfaces of HepG2 cells (human liver cell line) were modified using $NaIO_4$ to generate aldehyde handles on the cell surfaces, by adding $NaIO_4$ to a cell suspension in a tube and incubating the resulting mixture for 15 minutes.

The modified cells were suspended in a culture medium. The cell density was about 5 to about 6 million cells/ml. The culture medium included DMEM, glucose, FCS, and penicillin/streptomycin.

A TIP linker was also dissolved in the culture medium. The TIP linker was a polymeric molecule formed of multiple hydrazides conjugated to a polyethyleneimine (PEI) backbone. The linker concentration was about 6 to about 8 µM.

A solution of the culture medium with the cells and TIP linker was passed through a micro-channel illustrated in FIG. 17 at room temperature. The microfluidic channel had dimensions of 1 cm (length)×0.6 mm (width)×0.1 mm (height). The microfluidic channel had two inlets and one outlet. An array of 0.03 mm×0.05 mm elliptical micro-pillars with 0.02 mm gaps was situated in the center of the microfluidic channel, defining a cell residence compartment (growth region) that was 0.2 mm wide.

The solution was passed through the channel at various flow rates The fluid flow was driven by withdrawal of the fluid at the outlet end of the micro-channel.

Figure 4:
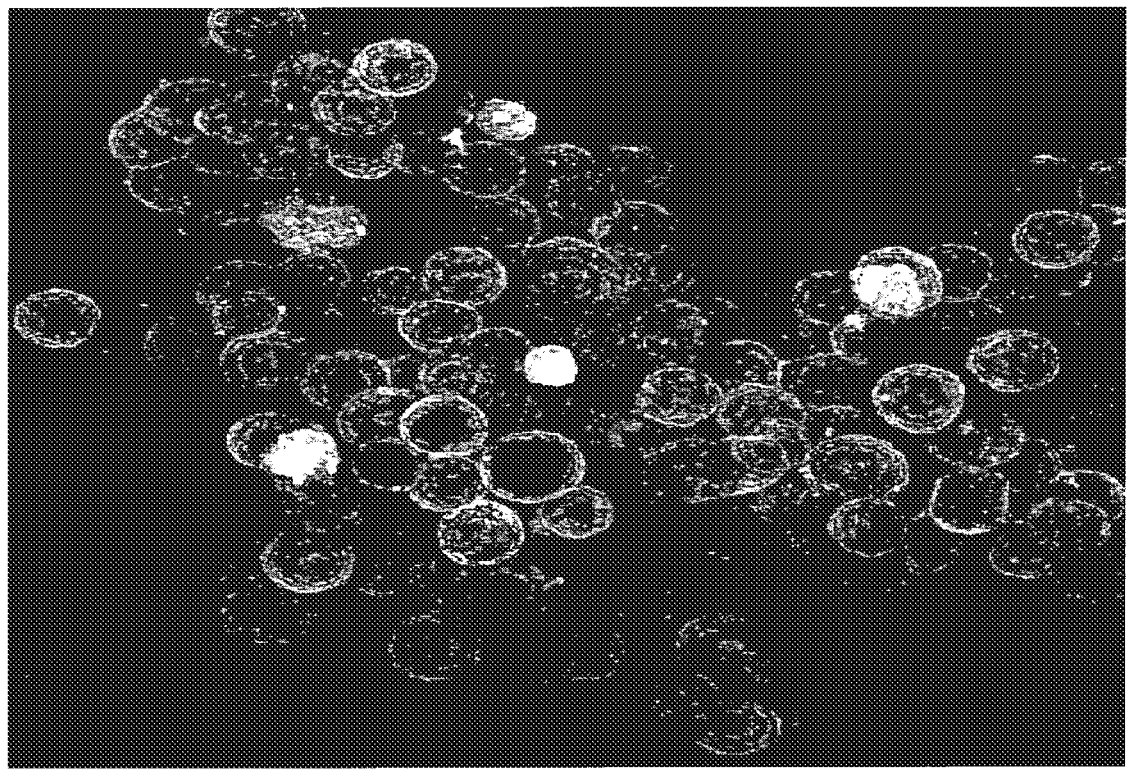
FIG. 4 is a confocal image of a representative 3D cellular aggregate formed according to an embodiment of the present invention.

It was observed that aggregation of cells formed in the cell-growth region. A confocal image of a representative cell aggregate is shown in FIG. 4. To visualize the presence of the linker on the cell surfaces, a linker conjugated with a fluorescent dye was used. The linker is shown in FIG. 4 as white circular regions around the cells. As can be seen in FIG. 4, many cells were encapsulated by the linker molecules and some of these encapsulated cells were in contact with one another, illustrating three-dimensional inter-cellular support effected by the linker.

Figure 5:
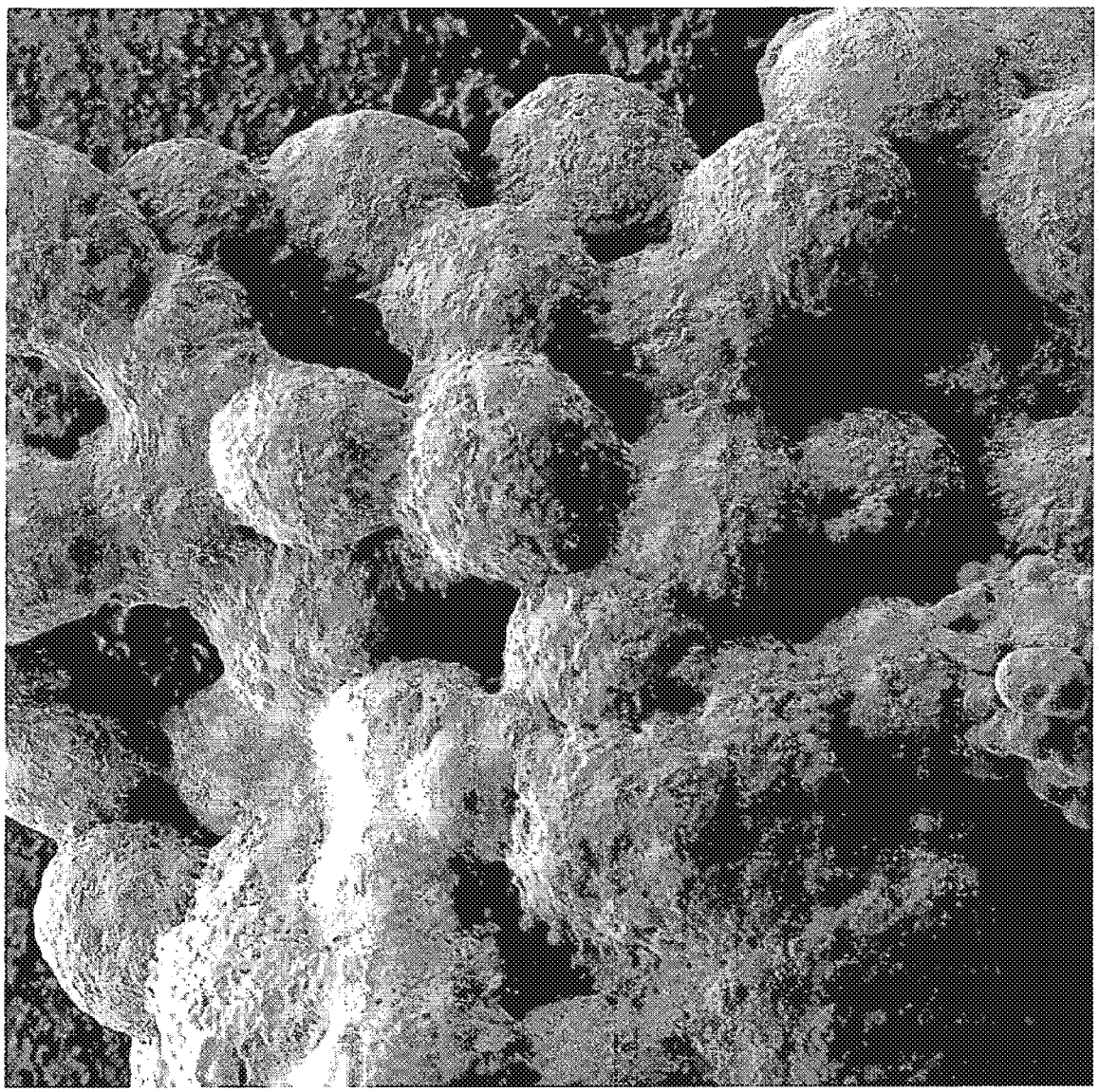
FIG. 5 is a scanning electron micrograph (SEM) of a representative 3D cellular aggregate formed according to an embodiment of the present invention.

An SEM image of the cellular aggregate is shown in FIG. 5, with the transient linker being present but invisible to the eye.

Figure 6:
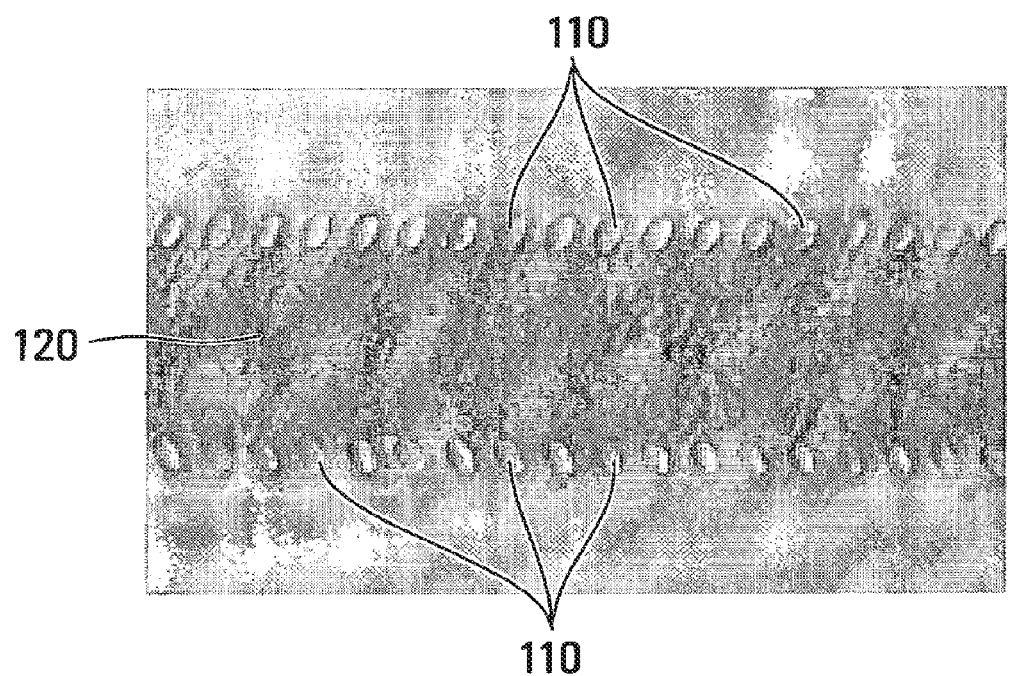
FIG. 6 is a transmission light image of a representative cell structure formed in a micro-fluid channel according to an embodiment of the present invention.

After about five minutes, a cellular structure was formed in the cell-growth region defined by the micro-pillars. A transmission light image of a representative cell structure formed in the micro-channel at a flow rate of about 0.03 ml/h is shown in FIG. 6.

After seeding had been completed, a culture medium without the TIP linker and cells was flowed through the fluid channel. A bar-shaped cell structure with a generally rectangular cross-section was formed.

Example II

Figure 7:
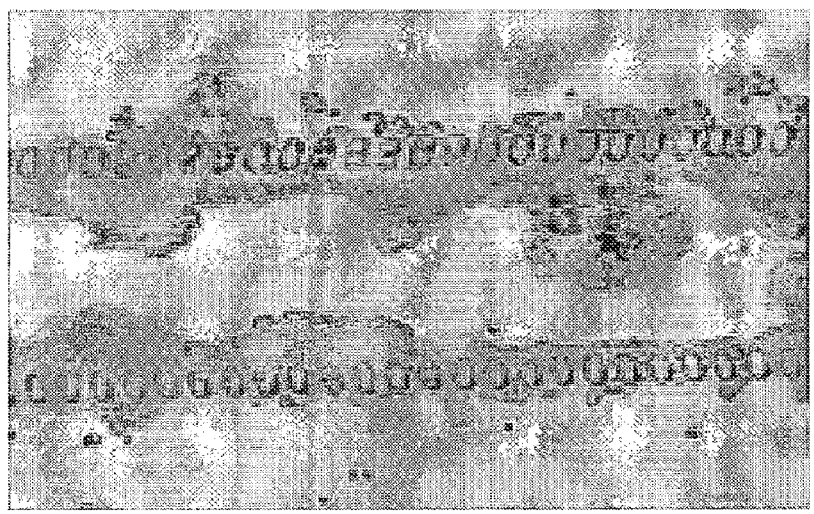
FIG. 7 is a transmission light image of a comparative cell structure formed in the micro-fluid channel of FIG. 6 but under different conditions.
Figure 8:
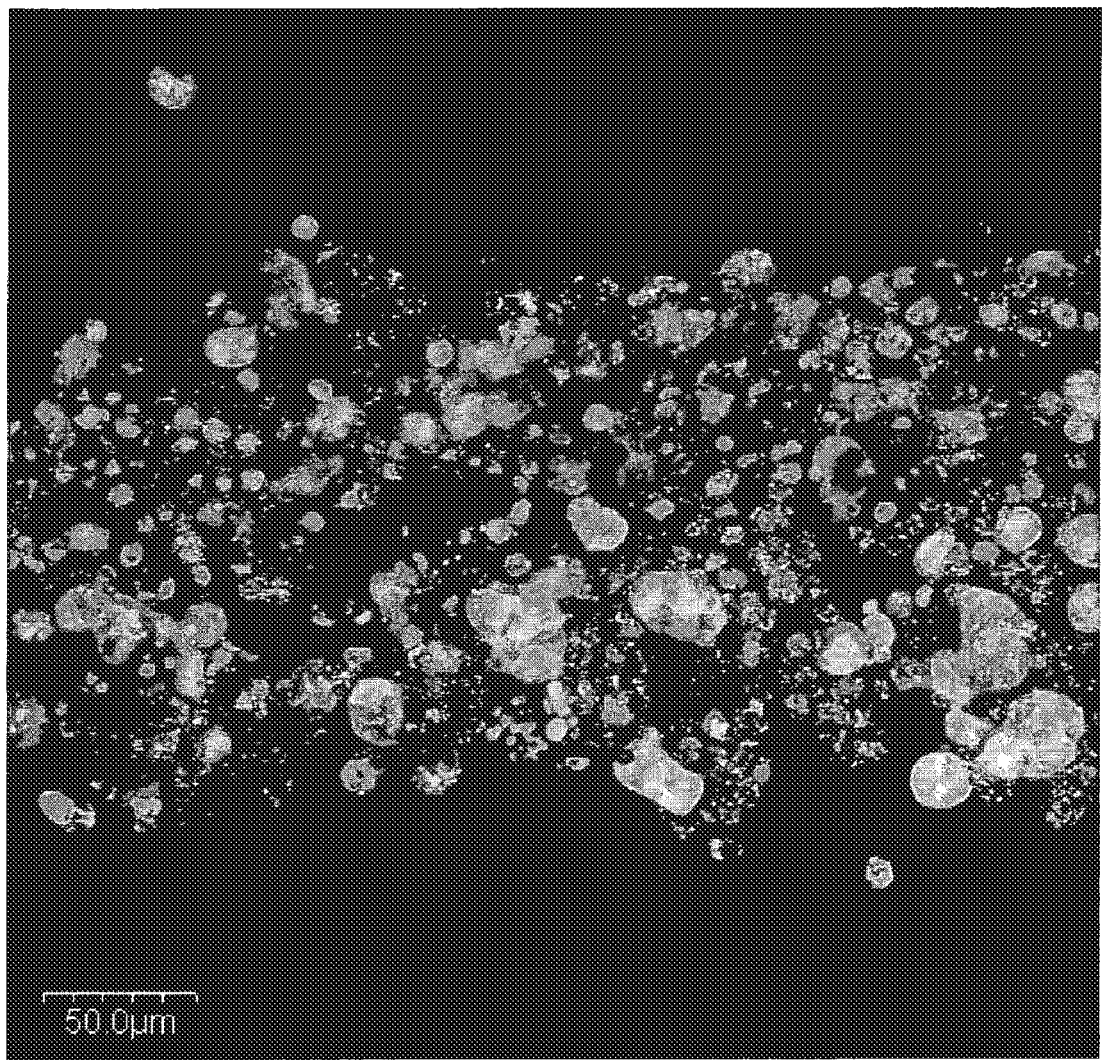
FIGS. 8 to 11 are confocal images of representative cell structures formed at different flow rates.
Figure 9:
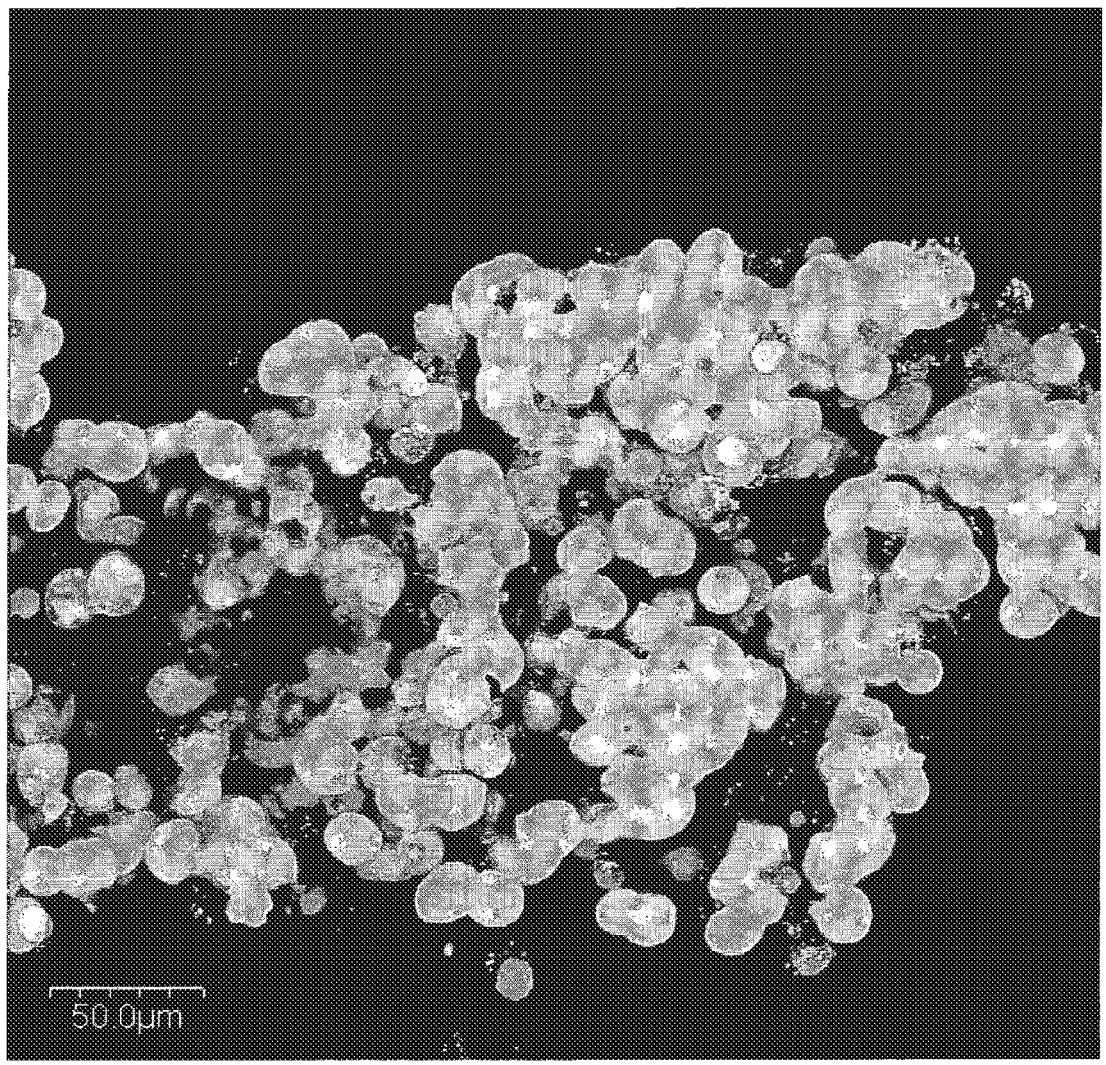
Figure 10:
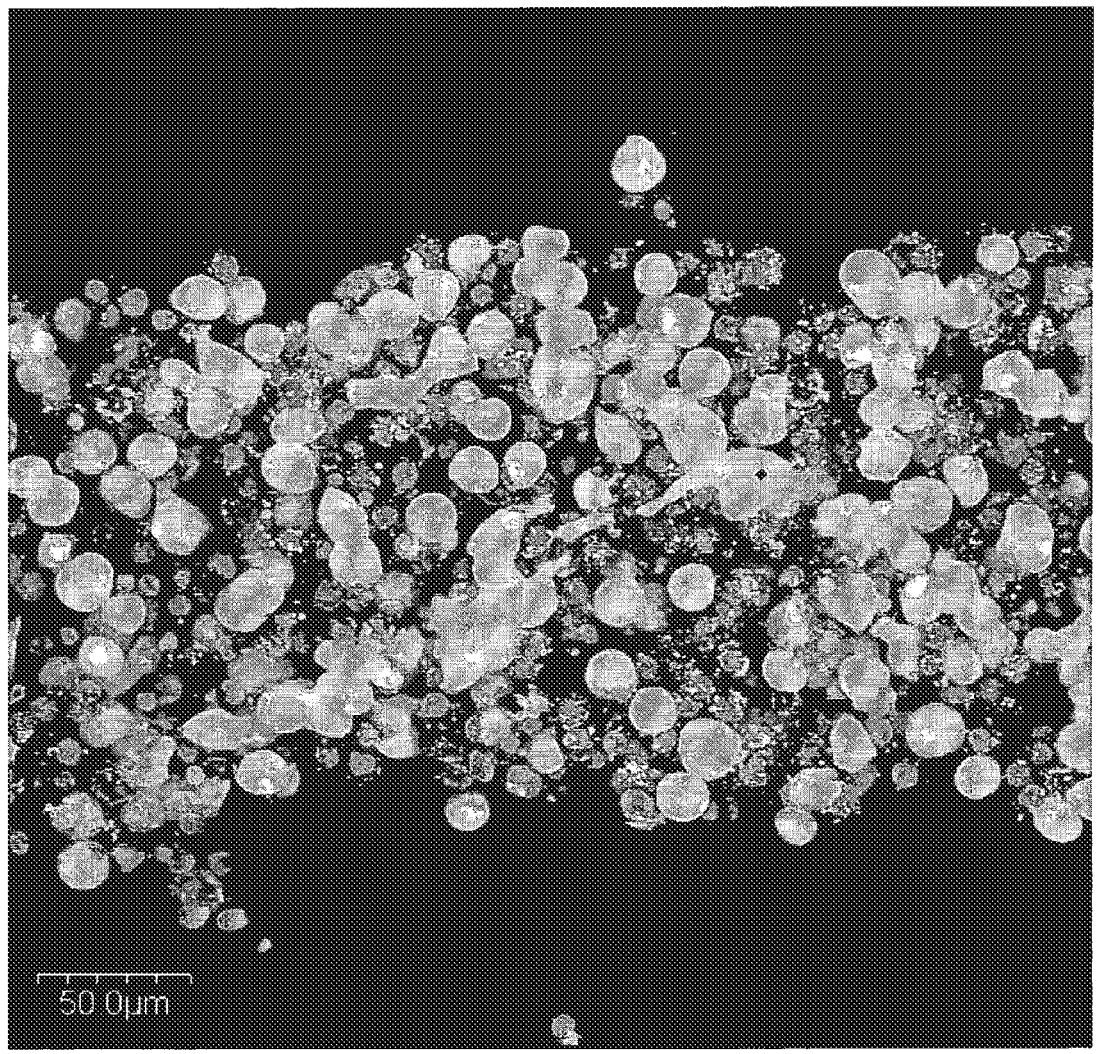
Figure 11:
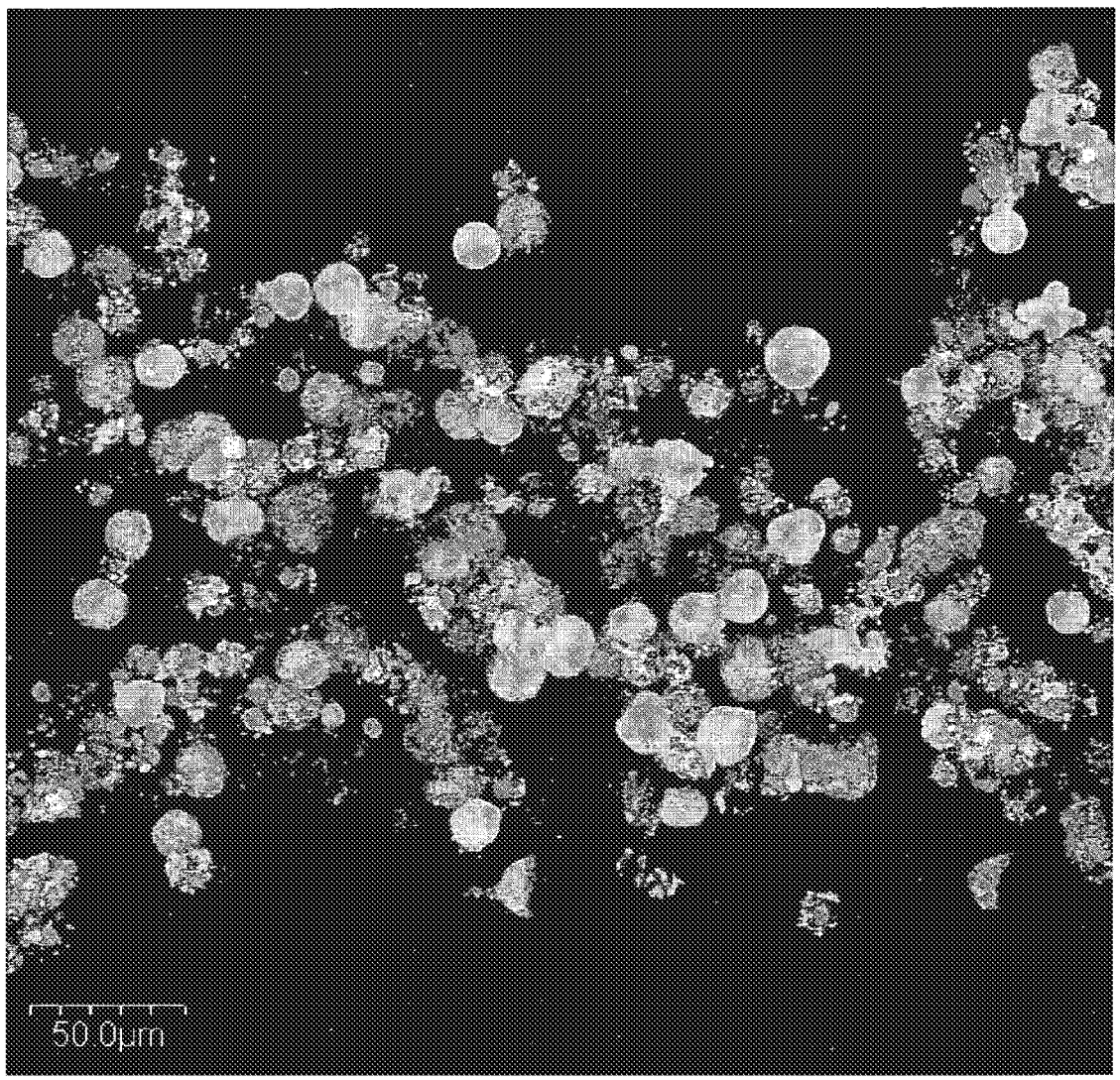

A comparative cell structure was formed as in Example I except that the aggregation conditions were different. In particular, the flow rate was relatively low for the given cell density and TIP linker concentration. FIG. 7 shows a transmission light image of this cell structure. As can be seen, under these conditions, the gaps between the pillars were clogged by cell aggregates. As a result, the formed structure did not have well-defined shape and dimension.

Example III

Cellular structures were formed as in Example I, except that the flow rate was varied to determine the optimal perfusion flow rate for the particular device and cell samples tested.

Each cellular construct was formed by flowing the cell culture medium at a flow rate selected from 0.01, 0.03, 0.06, or 0.22 ml/hr for one day.

The resulting structures were assessed with fluorescence viability staining. The live cells were stained with Calcein AM. The dead cells were stained with propidium iodide.

FIGS. 8, 9, 10 and 11 show confocal images of representative cell structures formed at the flow rate of 0.01, 0.03, 0.06 and 0.22 ml/hr respectively.

Figure 12:
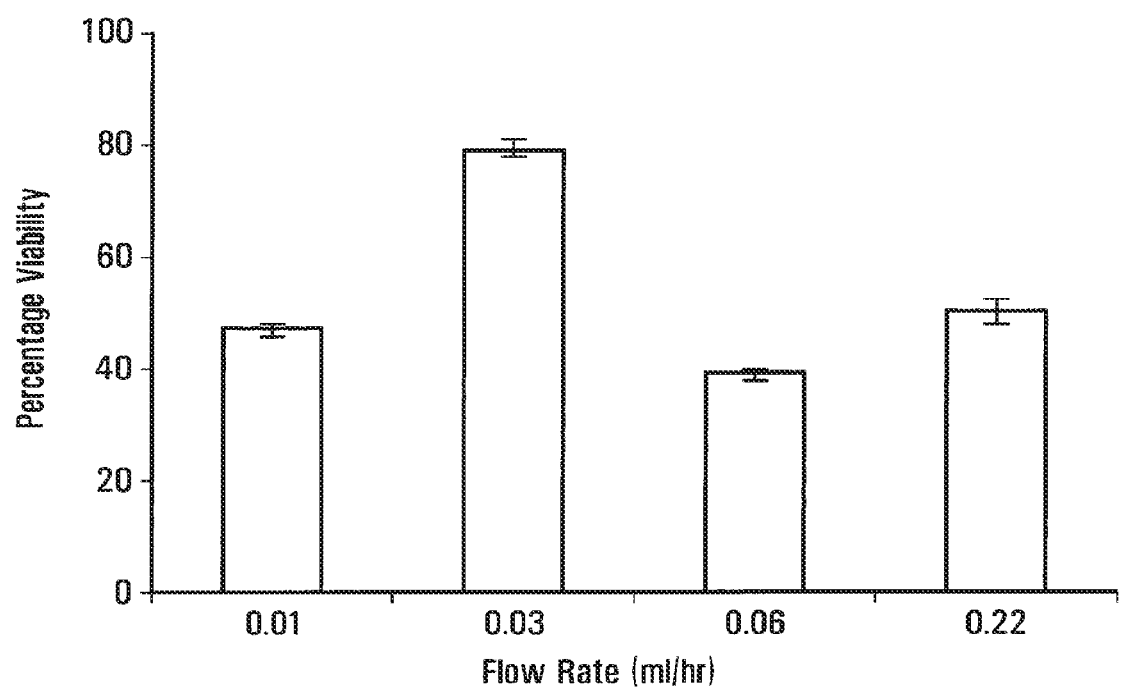
FIG. 12 is a bar graph showing the dependence of the percentage of viable cells on the flow rate.

The viability of the cells at different flow rates is shown in FIG. 12. As can be seen, for this particular arrangement and these cells, the viability was highest (about 80%) at the flow rate of 0.03 ml/hr. At the other flow rates, the viability was about 50%.

Without being limited to any particular theory, it may be expected that at too high a flow rate, a high shear or pressure exerted on the cells can cause reduction in viability; and at too low a flow rate, insufficient mass transport (of nutrients) can cause reduction in viability.

Example IV

Anchorage-dependent cells (HepG2 and rat bone marrow stem cells) were used to form cellular structures in a similar procedure as described in Example I, with a flow rate of 0.03 ml/hr, and were cultured for three or 14 days. It was observed that the 3D cell structures were adequately supported in the micro-channel for a period of up to two weeks.

The viability of the cells were assessed using fluorescence viability staining. Maintenance of the 3D morphology of the structures was assessed using F-actin staining.

The results showed excellent viability and maintenance of 3D morphology after 3 or 14 days of culture, respectively.

Figure 13:
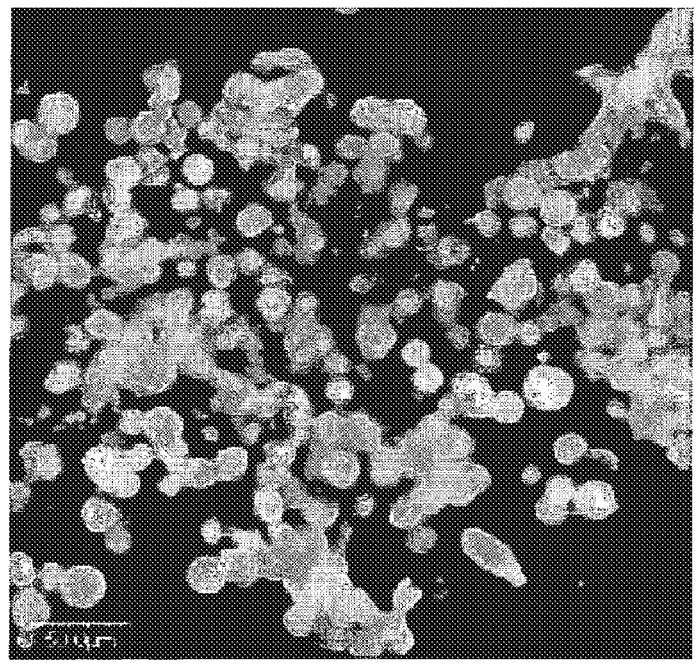
FIG. 13 is a confocal image of a perfusion cell culture of HepG2 cells in a fluid channel, formed according an embodiment of the present invention.
Figure 14:
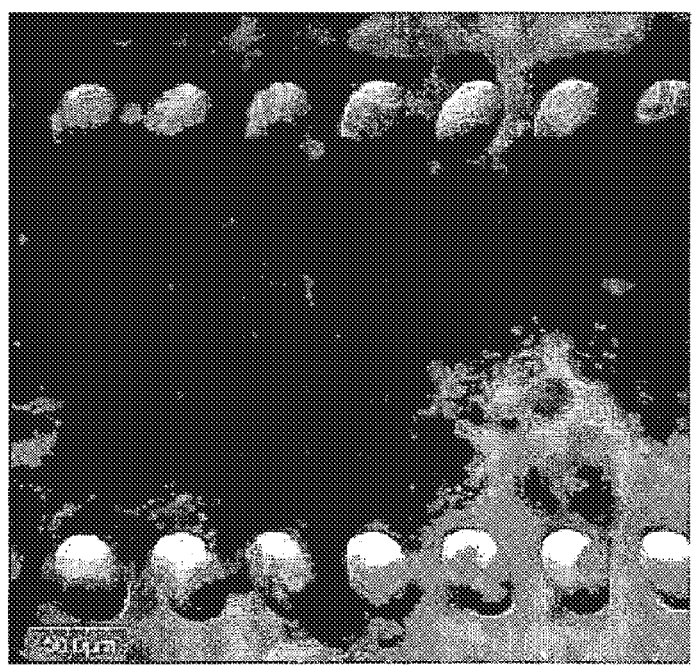
FIG. 14 is a transmission light image of the cell culture of FIG. 13.

FIG. 13 is a confocal image of a representative cell structure formed of HepG2 cells after 3 days of culture. FIG. 14 is an SEM image of the same cell structure in the micro-channel.

FIG. 15 is a confocal image of a representative cell structure formed of primary rat BMSC cells after 14 days of culture. FIG. 16 is an SEM image of the same cell structure in the micro-channel.

Confocal images of actin staining of the sample cell structures (not shown) also showed that the cortical actin distribution in the sample structures was typical of a 3-D morphology.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method of forming a cellular structure, comprising:
supplying cells and a transient linker to a volume partially enclosed by a cage, said linker facilitating initial attachment of adjacent cells to form a cell aggregate, said cage defining distributed openings that are sized to retain said cell aggregate;
supplying a fluid comprising a cell culture medium to said volume;
withdrawing said fluid from said volume through said openings; and
culturing aggregated cells retained in said volume to form a cell structure.

2. The method of claim 1, wherein said cells are suspended in said fluid and said linker is dissolved in said fluid before said fluid is supplied to said volume.

3. The method of claim 1, comprising maintaining a flow of said fluid through said volume.

4. The method of claim 3, wherein said cells in said fluid have a density of about 5 to about 6 million cells/ml and said transient linker in said fluid has a concentration of about 6 to about 8 μM.

5. The method of claim 1, wherein said openings are distributed to facilitate perfusion of said cell culture medium through said cell structure.

6. The method of claim 1, wherein said cage is disposed in a conduit, and said fluid flows through said conduit.

7. The method of claim 6, wherein said conduit comprises a bottom and opposing side walls extending from said bottom.

8. The method of claim 7, wherein said cage comprises a plurality of projections extending from said bottom and between said side walls.

9. The method of claim 8, wherein said projections comprise micro-pillars.

10. The method of claim 9, wherein said micro-pillars are arranged in a substantially U-shaped pattern.

11. The method of claim 10, wherein a gap between two adjacent ones of said micro-pillars is about 10 to about 50 micrometers.

12. The method of claim 1, wherein said linker comprises a polyethyleneimine backbone and hydrazide groups bonded to said backbone.

13. The method of claim 12, wherein said linker has a molecular weight of about 2000 to about 20000 Dalton.

14. The method of claim 1, wherein said cells comprise an aldehyde group.

15. The method of claim 14, wherein said cells comprise cells that have been modified to form aldehyde groups on surfaces of said modified cells.

16. The method of claim 1, wherein said cells comprise HepG2 cells or rat bone marrow stem cells.

17. The method of claim 3, wherein said flow of said fluid is actuated by applying a withdrawal force downstream of said distributed openings.

18. A cell culturing device, comprising:
a conduit;
a fluid flowing in said conduit, said fluid comprising cells, a transient linker and a cell culture medium, said linker facilitating initial attachment of adjacent cells to form a cell aggregate; and
a cage in said conduit for retaining aggregated cells formed in said fluid, said cage defining distributed openings that are sized to retain said aggregated cells and allow said fluid to flow through.

19. The device of claim 18, wherein said cage comprises a plurality of projections, arranged in a substantially U-shaped pattern.

20. The device of claim 19, wherein said projections comprise micro-pillars.

21. The device of claim 19, wherein said conduit has a bottom and opposing side walls extending from said bottom, said projections extending from said bottom.

22. The device of claim 18, wherein said cells in said fluid have a density of about 5 to about 6 million cells/ml and said transient linker in said fluid has a concentration of about 6 to about 8 μM.

23. The device of claim 18, wherein said cells are suspended in said fluid.

24. The device of claim 18, wherein said linker is dissolved in said fluid.

25. The device of claim 18, wherein said linker comprises a polyethyleneimine backbone and hydrazide groups bonded to said backbone.

26. The device of claim 25, wherein said linker has a molecular weight of about 2000 to about 20000 Dalton.

27. The device of claim 18, wherein said cells comprise an aldehyde group.

28. The device of claim 27, wherein said cells comprise cells that have been modified to form aldehyde groups on surfaces of said modified cells.

29. The device of claim 18, wherein said cells comprise HepG2 cells or rat bone marrow stem cells.

30. The device of claim 18, wherein said fluid is actuated by a withdrawal force applied downstream of said distributed openings.

* * * * *